United States Patent
Kavteladze

(10) Patent No.: US 10,219,707 B2
(45) Date of Patent: *Mar. 5, 2019

(54) DEVICE FOR MEASUREMENT OF PRESSURE AND ADMINISTRATION OF DRUGS IN AN ANEURYSM IN A BLOOD VESSEL

(71) Applicant: Zaza Alexandrovich Kavteladze, Moscow (RU)

(72) Inventor: Zaza Alexandrovich Kavteladze, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,612

(22) PCT Filed: Oct. 2, 2013

(86) PCT No.: PCT/RU2013/000873
§ 371 (c)(1),
(2) Date: Apr. 17, 2015

(87) PCT Pub. No.: WO2014/062089
PCT Pub. Date: Apr. 24, 2014

(65) Prior Publication Data
US 2015/0257657 A1    Sep. 17, 2015

(30) Foreign Application Priority Data
Oct. 18, 2012  (RU) ................. 2012144358

(51) Int. Cl.
A61B 5/02     (2006.01)
A61B 5/0215   (2006.01)
(Continued)

(52) U.S. Cl.
CPC ........ *A61B 5/0215* (2013.01); *A61B 5/02014* (2013.01); *A61B 5/4839* (2013.01);
(Continued)

(58) Field of Classification Search
CPC . A61B 5/02014; A61B 5/0215; A61B 5/6862; A61F 2/856
See application file for complete search history.

(56) References Cited

U.S. PATENT DOCUMENTS 5,037,403 A    8/1991   Garcia
5,716,365 A    2/1998   Goicoechea et al.
(Continued)

FOREIGN PATENT DOCUMENTS

RU    2192810 C2   11/2002
RU      61120 U1    2/2007
(Continued)

OTHER PUBLICATIONS

May 11, 2016—(EP) Supplementary European Search Report—App 13847821.
(Continued)

*Primary Examiner* — Puya Agahi
(74) *Attorney, Agent, or Firm* — Banner & Witcoff, Ltd.

(57) ABSTRACT

The invention relates to medicine, in particular, to vascular and endovascular surgery. The objective of the invention is to measure pressure and to administer drugs to an aneurysm in a blood vessel after implantation of a stent-graft. The device for measurement of pressure and for administration of drugs is made of a shape memory material, in the form of a hollow tube with side apertures.

3 Claims, 1 Drawing Sheet

(51) Int. Cl.
*A61B 5/00* (2006.01)
*A61M 25/00* (2006.01)
*A61F 2/88* (2006.01)

(52) U.S. Cl.
CPC ....... *A61B 5/6862* (2013.01); *A61M 25/0043* (2013.01); *A61B 2560/04* (2013.01); *A61B 2562/0247* (2013.01); *A61F 2/88* (2013.01); *A61F 2250/0068* (2013.01)

(56) References Cited

U.S. PATENT DOCUMENTS

| | | | |
|---|---|---|---|
| 6,360,749 | B1 | 3/2002 | Jayaraman |
| 6,840,956 | B1 | 1/2005 | Wolinsky et al. |
| 2005/0187482 | A1* | 8/2005 | O'Brien ............... A61B 5/0031 600/486 |
| 2007/0162106 | A1 | 7/2007 | Evans et al. |
| 2007/0168011 | A1* | 7/2007 | LaDuca .................... A61F 2/95 623/1.11 |
| 2007/0239261 | A1 | 10/2007 | Bose et al. |
| 2008/0004692 | A1 | 1/2008 | Henson et al. |
| 2008/0097297 | A1 | 4/2008 | Kelley et al. |
| 2008/0234809 | A1 | 9/2008 | Greenan |
| 2011/0067778 | A1 | 3/2011 | Mitchell et al. |
| 2011/0230952 | A1* | 9/2011 | Kassab ............ A61B 17/12113 623/1.11 |
| 2012/0101510 | A1 | 4/2012 | Lenker et al. |
| 2013/0289690 | A1* | 10/2013 | Thapliyal .................. A61F 2/90 623/1.2 |

FOREIGN PATENT DOCUMENTS

| | | |
|---|---|---|
| RU | 2009119849 A | 11/2010 |
| RU | 2462197 | 8/2012 |
| RU | 2011105185 A | 8/2012 |
| RU | 2460500 C1 | 9/2012 |
| SU | 260101 | 12/1969 |
| WO | 9809583 | 3/1998 |
| WO | 02058551 A2 | 8/2002 |
| WO | 2006055443 A2 | 5/2006 |
| WO | 2006058042 A2 | 6/2006 |
| WO | 2009/048372 A1 | 4/2009 |
| WO | 2009132396 A1 | 11/2009 |
| WO | 2010068467 A1 | 6/2010 |

OTHER PUBLICATIONS

Jan. 16, 2014 (WO) International Search Report—International application PCT/RU2013/000873.

* cited by examiner

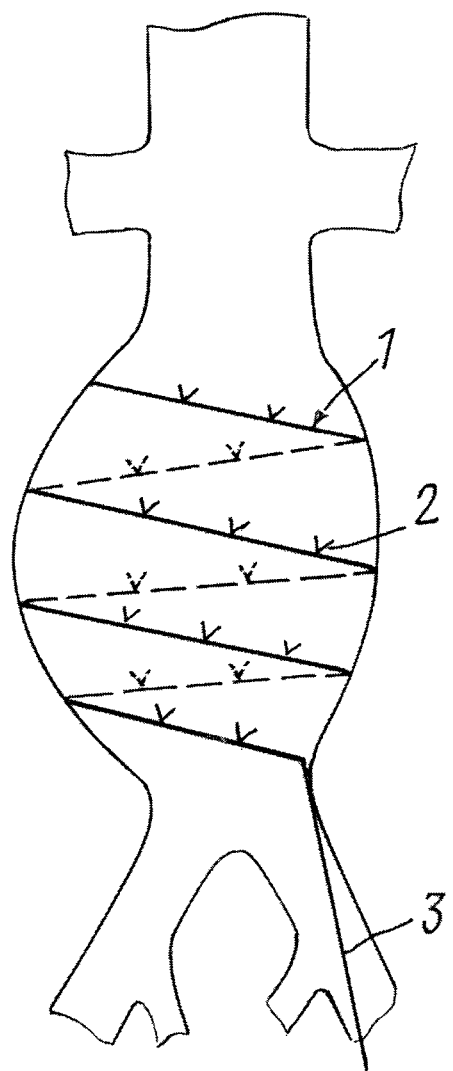

DEVICE FOR MEASUREMENT OF PRESSURE AND ADMINISTRATION OF DRUGS IN AN ANEURYSM IN A BLOOD VESSEL

CROSS-REFERENCE TO RELATED APPLICATIONS

This application is a U.S. National Stage application under 35 U.S.C. § 371 of International Application PCT/RU2013/000873 (published as WO 2014/062089 A1), filed Oct. 2, 2013, which claims priority to Application RU 2012144358, filed Oct. 18, 2012. Benefit of the filing date of each of these prior applications is hereby claimed. Each of these prior applications is hereby incorporated by reference in its entirety.

The invention relates to medicine, in particular, to vascular and endovascular surgery.

A stent-graft providing internal isolation of an aneurysm in a blood vessel is known (see U.S. Pat. No. 5,716,365, A61F, 1998). A disadvantage of the stent-graft is in impossibility of assessing the condition of an isolated aneurysmal sac after the graft implantation (in particular, impossibility of measuring of intra-aneurysm sac pressure and administering drugs, as far as necessary).

A device for measurement of pressure and for administration of drugs is known (see U.S. Pat. No. 5,037,403, A61M 25/00, 1991), wherein the device is made in the form of a catheter with side apertures. Said device is the closest technical solution in terms of the problem to be solved.

A disadvantage of the known technical solution is in impossibility of assessing the condition of an isolated space of an aneurysmal sac between the aneurysmal vessel wall and the wall of a stent-graft after the implantation of the latter.

The objective of the invention is to eliminate the above disadvantages and develop a device allowing assessment of the condition of an isolated space of an aneurysmal sac by measuring pressure and administering drugs to an aneurysm in a blood vessel after implantation of a stent-graft.

The objective is achieved by providing a device for measurement of pressure and for administration of drugs made in the form of a hollow tube with side apertures, the device being made of a shape-memory material—nitinol—that provides changing the shape of the tube when the latter is introduced into an aneurysm in a blood vessel and filling the entire interior space of the aneurysm at its circumference, and wherein the tube is adapted to be connected to a pressure-measuring sensor and to administer drugs through a detachable hollow tube.

The FIGURE shows a general view of the claimed invention.

In the claimed invention the device for measurement of pressure and for administration of drugs is made in the form of hollow tube 1 with side apertures 2. Hollow tube 1 is made of nitinol, i.e. a shape-memory material, and is adapted to be connected to a pressure-measuring sensor (not shown) and to administer drugs through detachable hollow tube 3.

The device is used as follows:

Before introduction of the device into the aorta an aneurysm in a blood vessel is diagnosed to determine its shape and size. The shape and size of nitinol-made hollow tube 1 is specified on the basis of the diagnostic results, and then the tube is introduced into the aneurysm in the blood vessel by one of known methods. The shape-memory material allows hollow tube 1 to fill the entire interior space of the aneurism at its circumference. After that a stent-graft is implanted by a known method. Measurement of pressure and, if necessary, administration of drugs, for example Thrombovar, are performed through detachable hollow tube 3 disposed in the aneurysmal sac between the vessel wall and the wall of the stent-graft, by using side apertures 2. Hollow tube 3 is removed also by a known method.

Thus, the design of the device for measurement of pressure and for administration of drugs to an aneurysm in a blood vessel, made in the form of a hollow tube having shape memory allows qualitative measurement of pressure and qualitative administration of drugs due to filling by the hollow tube the interior space of the aneurysm at its circumference.

The invention claimed is:

1. A device for measurement of pressure in an isolated space of an aneurysmal sac between an aneurysmal vessel wall and a wall of a stent-graft and for administration of drugs in said aneurysmal sac, wherein the device comprises
    a first hollow tube with side apertures, wherein said first hollow tube is made of nitinol and is shaped and sized to conform to the aneurysmal sac at its circumference when introduced into the aneurysmal sac, said first hollow tube forming coils against said aneurysmal vessel wall, and
    a second hollow tube, configured to be removably attached to both the first hollow tube and a pressure-measuring sensor to measure pressure between said aneurysmal vessel wall and said wall of the stent-graft, wherein the second hollow tube is further configured for administration of drugs through said second hollow tube.

2. The device of claim 1, wherein the side apertures are positioned towards an interior of said aneurysmal sac.

3. A method for treating an aneurysm, comprising:
    on a basis of a determination of a shape and size of an aneurysmal sac of the aneurysm, shaping and sizing the first hollow tube of the device of claim 1;
    introducing the first hollow tube into the aneurysm, to adopt a coiled shape against an aneurysmal vessel wall;
    implanting a stent-graft within the aneurysmal sac and within the coiled shape of the first hollow tube, to form an isolated space between the aneurysmal vessel wall and a wall of the stent-graft; and
    connecting the second hollow tube of the device to the first hollow tube, the second hollow tube being configured, via said side apertures of said first hollow tube, for administration of a drug into said isolated space.

* * * * *